United States Patent
Kalb et al.

[11] Patent Number: 5,192,271
[45] Date of Patent: Mar. 9, 1993

[54] DEVICE AND METHOD FOR EFFECTING AN ERECTION

[76] Inventors: Irvin M. Kalb, 327 Alta Ave., Santa Monica, Calif. 90406; Robert H. Shaw, 243 Peck Dr., Beverly Hills, Calif. 90212; Michael J. Ram, 1 Horseshoe Rd., Bell Canyon, Calif. 91307

[21] Appl. No.: 797,319

[22] Filed: Nov. 25, 1991

[51] Int. Cl.⁵ .......................... A61M 5/00; A61F 5/00
[52] U.S. Cl. .................................... 604/116; 600/38; 128/DIG. 6; 128/883
[58] Field of Search .............. 128/79, 883, DIG. 6, 128/DIG. 26, 386; 606/130; 604/93, 116, 117, 180, 46; 600/38-41

[56] References Cited

U.S. PATENT DOCUMENTS

| | | | |
|---|---|---|---|
| 853,410 | 5/1907 | Huebner | 128/79 |
| 3,167,072 | 1/1965 | Stone et al. | 604/116 X |
| 3,794,020 | 2/1974 | Bagby | 128/79 |
| 3,957,048 | 5/1976 | Jacobs | 604/180 |
| 4,127,118 | 11/1978 | Latorre | 128/79 |
| 4,150,669 | 4/1979 | Latorre | 128/79 |
| 4,314,568 | 2/1982 | Loving | 604/116 X |
| 4,844,061 | 7/1989 | Carroll | 604/180 X |
| 5,027,800 | 7/1991 | Rowlands | 128/79 |

Primary Examiner—Mickey Yu
Assistant Examiner—Brian E. Hanlon
Attorney, Agent, or Firm—Michael J. Ram

[57] ABSTRACT

A device for delivering an erection causing stimulus to the penis comprising a ring for placement of the penis. In one variation of the device the ring includes a needle guide projecting from the surface of the ring. In a second variation the ring includes a porous drug delivery media attached to the inner surface of the ring. In a third variation the ring has an electrically conductive material attached to the inner surface of the ring.

16 Claims, 2 Drawing Sheets

DEVICE AND METHOD FOR EFFECTING AN ERECTION

BACKGROUND

The present invention relates to a device and method for delivering a stimulus to a flaccid penis to produce, enhance, or sustain an erection.

Because of psychological or physiological reasons many older males as well as some younger men suffer from impotency. Impotency is generally defined as the inability to attain an erection of the penis adequate to participate in coitus or sustain an adequate erection to allow the male to attain orgasm or ejaculation.

Many solutions to this problem have been suggested in the past including tourniquets, straps, bands, sleeves or other supportive devices, various different implantable devices, drugs and electrical stimulation. These various different procedures or devices have met varying success. Additionally, some of these techniques can be uncomfortable, inconvenient or dangerous to use, causing irreversible injury to the user. Devices which must be worn by the male during intercourse can interfere with the sexual act and be psychologically disturbing to the male as well as be painful or distracting to either or both of the participants. The implantable devices require a surgical procedure and therefore are not suitable for all males. Drugs, if not properly administered, will not only cause an erection but can also cause undesirable systemic responses such as severe headaches, breathing problems and heart irregularities.

Erection of the penis is caused by engorgement of the erectile tissue (the corpora cavernosa), a region of tissue along the sides and upper portion of the penis, with blood resulting in elongation, expansion, and stiffening of the penis. This engorgement may be caused by an increase of blood flow to the erectile tissue, a decrease in blood flow from the erectile tissue, or a combination of both.

A non-pharmaceutical approach has been the delivery of electrical stimulation through an electrode implanted in the cavernous nerve or an electrode tipped probe placed in the rectum of the male.

In spite of their disadvantages and side effects, drugs have been used most effectively to aid in generating an erection. Drugs and other substances which have been administered in the past include, testosterone and synthetic derivatives thereof, progesterone, yohimbine, damiana, ginseng, levadopa, hydergine, clomiphene, phosphorous, strychnine, cantharides, papaverine, hydralazine, sodium nitroprusside, pheoxybenzamine, and phentolamine.

No universally acceptable modality for the relief of impotency has been endorsed by the medical community. Various stimuli, including drugs and electrical stimulation, are presently utilized to at least temporarily (for a period adequate to perform sexual intercourse) relieve this problem. In spite of the lack of agreement on a preferred treatment modality, the number of prescriptions for erection enhancing drugs, particularly drugs for injecting directly into the tissue of the penis, has been rapidly increasing. However, there is no safe, reliable system available for injecting these drugs. As a result, the users are exposing themselves to the danger of overdose, and physical injury resulting from improper placement of the needle.

Thus, there is a need for a system which will allow discrete, safe, painless and reliable delivery of the stimulus which will bring about the desired, temporary relief of impotency. Preferably, the system should allow delivery of the stimulus prior to initiating the sexual encounter, and removal of the system so that it will not interfere either physically or psychologically with the performance of the male. As a minimum, the system should be unobtrusive and non-interfering if it must be retained in position to maintain the erection.

SUMMARY

The present invention is directed to a device and method that supplies these needs and eliminates the deficiencies of prior devices and systems.

The device of the invention comprises an open ring for temporary application to the penis which is particular designed for delivery of the desired stimulus. In one embodiment, the ring incorporates a needle guide for proper placement of a syringe delivered drug. In a second embodiment the ring includes an inner layer of a foam or microporous film which incorporates a drug composition suitable for transdermal delivery. A third embodiment includes a similar inner layer of foam or film material which is capable, either by its composition or by being filled with a conductive material, of delivering an electrical stimulus supplied by an external source.

In the embodiment designed for syringe delivery of a drug, the needle guide extending from the ring surface is angled to assure that the drug is delivered to the desired location in the erectile tissue.

DRAWINGS

These and other features, aspects and advantages of the present invention will become better understood from the following description, appended claims, and accompanying drawings where:

DESCRIPTION

Figure 1:
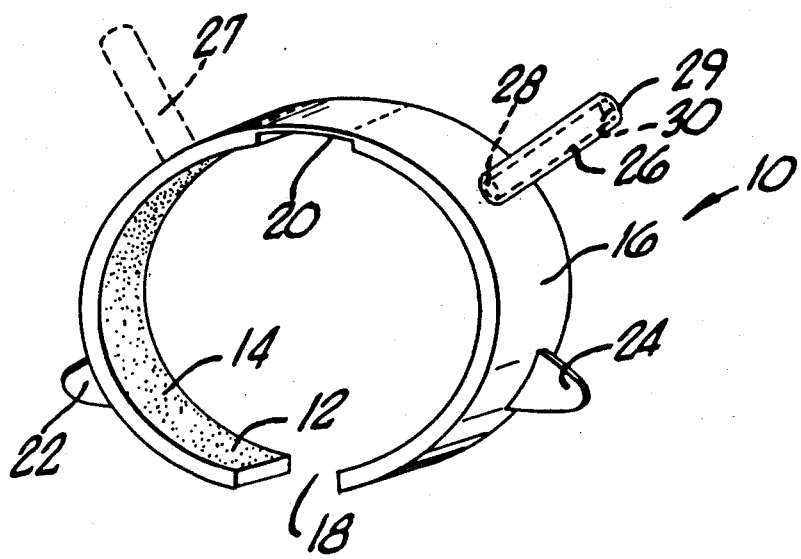
FIG. 1 is a front perspective view of a ring for drug delivery embodying features of the present invention.
Figure 2:
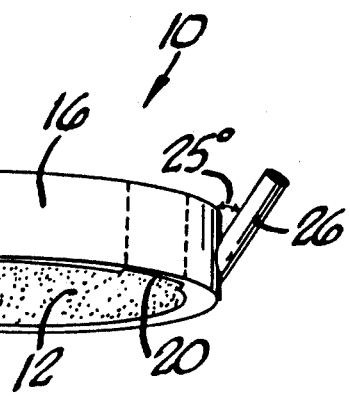
FIG. 2 is a side perspective view of the ring of FIG. 1.

FIGS. 1 and 2 show a version of the ring 10 for syringe delivery of drugs according to the present invention.

The ring 10 has a diameter chosen to be slightly less than the diameter of a flaccid male penis so that when applied to the penis the ring 10 will grasp the penis but will not restrict blood flow in the penis or cause pain to the user. In a preferred form the ring has both a flat inner and outer surface 14 and 16. Addition of a tissue compatible tacky or adhesive material 12 to the inner surface 14 of the ring 10 will aid in preventing the ring 10, when applied to the penis, from slipping or rotating from its desired position.

In order to ease placement of the ring 10 onto the penis, the ring 10 has a break 18 extending completely across the ring 10. The ring 10 has a flexible portion 20 approximately 180° from the break 18 which renders the ring capable of bending. Suitable flexibility can be accomplished by forming the portion 20 with a thickness less than that of the rest of the ring, creating a living hinge in the portion 20, corrugated the portion 20 or constructing the portion 20 of a different, more flexible material. In the alternative, the ring 10 may be formed from a flexible material that allows flexing and bending without the addition of a separated flexible portion.

Placement of the ring 10 is accomplished by expanding the ring diameter by pulling apart the ring halves at the break 18, this action being aided by the presence of the flexible portion 20. This spreading action is further aided by the presence of a left and right tab 22 and 24 attached to the ring, the left tab 22 being located on one side of the break 20 and the right tab 24 being located on the other side of the break 20, each tab being easily grasped between the fingers of the user of the ring 10.

Extending from the outer surface 16 of the ring 10, preferably midway across the width of the ring, and spaced from the flexible portion are a right or left extension tube 26 and 27. The tubes 26 and 27 are preferably angled from the outer surface 16 of the ring 10 so that when the ring 10 is applied to the penis the outer end 29 of the tube 26 points away from the abdomen of the user, preferably oriented in a plane perpendicular to the sides of the ring. The angle of the tube is selected so that a syringe needle placed through the tube 26 or 27 penetrates only through the penile erectile tissue and does not enter the other tissue of the penis. The penile erectile tissues extend along the length of the upper sides of the penis. The orientation of the tubes 26 and 27 are chosen so that the tubes, when the ring is placed on the penis, point approximately in the same direction as the erectile tissue. The angle of the tubes 26 and 27 to the surface of the ring 10 may be from about 10 to 75 degrees with a preferred angle being from about 15 to about 45 degrees; a more preferred angle being 25 degrees. The ring 10 at the point of attachment of the extension tube 26 has a hole 28 through its surface, the hole coinciding with the internal bore 30, so that a needle placed inside the bore 30 of the tube 26 can penetrate beyond the inner surface 14 of the ring 10. The ring 10 may be constructed with a single extension tube 26 on either side of the flexible portion 20 or two extension tubes 26 and 27, one on each side of the flexible portion 20.

Figure 3:
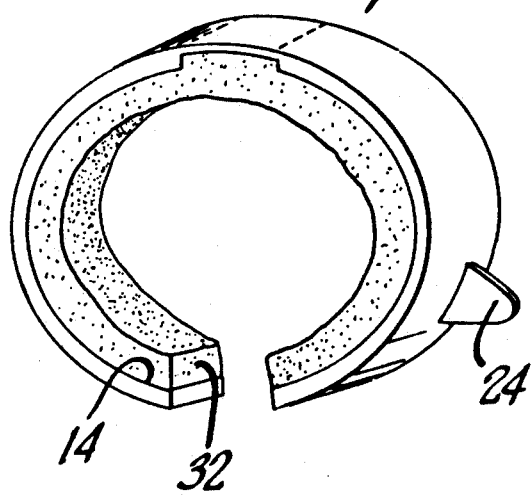
FIG. 3 is a front perspective view of a ring for transdermal delivery of drugs embodying features of the present invention.
Figure 4:
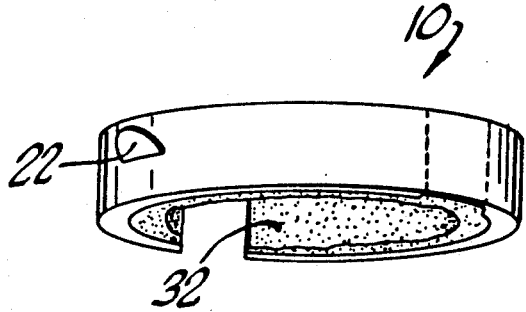
FIG. 4 is a side perspective view of the ring of FIG. 3.

FIGS. 3 and 4 shows a ring 10 of similar construction except that the extension tubes 26 or 27 are not present. Added to the inner surface 14, in place of the adhesive 12, is a coating 32, which may also have adhesive characteristics, which has the capacity to release, at a predetermined rate, an erection stimulating pharmaceutical. Suitable drug delivery media includes dimethyl sulfoxide, viscolelastics such as hyaluronic acid, glycerine compounds, saline solutions and solutions of polyvinyl alcohol, hydroxyl ethyl methyl cellulose or methyl cellulose.

Figure 5:
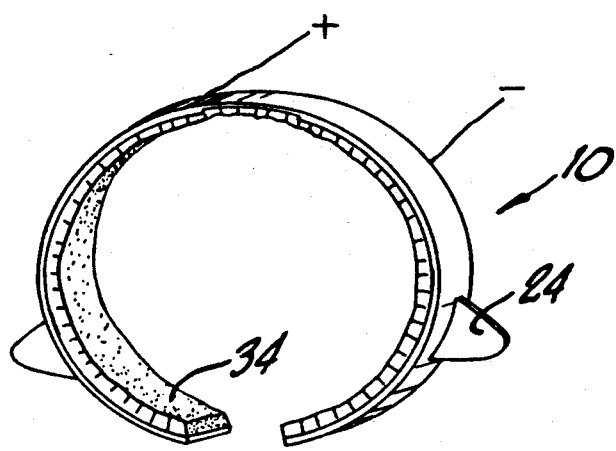
FIG. 5 is a front perspective view of a ring for delivery of an electrical stimulus embodying features of the invention.
Figure 6:
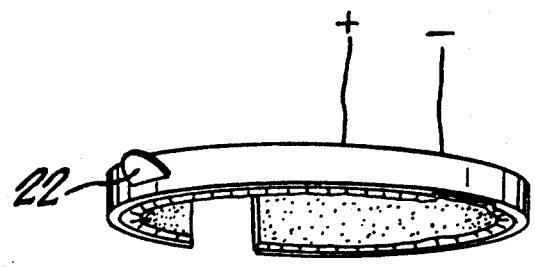
FIG. 6 is a side perspective view of the ring of FIG. 5.

FIGS. 5 and 6 likewise show a ring 10 of similar construction to the ring 10 of FIGS. 1 and 2 wherein the adhesive 12 is replaced by an electrically conductive material 34, which may also be conductive, for delivery of an erection stimulating electrical current to the penis. Suitable electrically conductive materials includes conductive media applied to the skin contacting surface of disposable EKG electrodes. The electrical charge can be delivered from an external source through wires 36 and 38 connected to the electrically conductive material 34 or a electrical energy storage cell such as a battery, capacitor or other suitable source of electrical energy external to the ring or incorporated in the ring structure. While it is possible that a suitable erection can be obtained by the delivery of a single dose of energy, it may be necessary, to sustain an erection, that the electrical delivery ring be retained on the penis during coitus.

Figure 8:
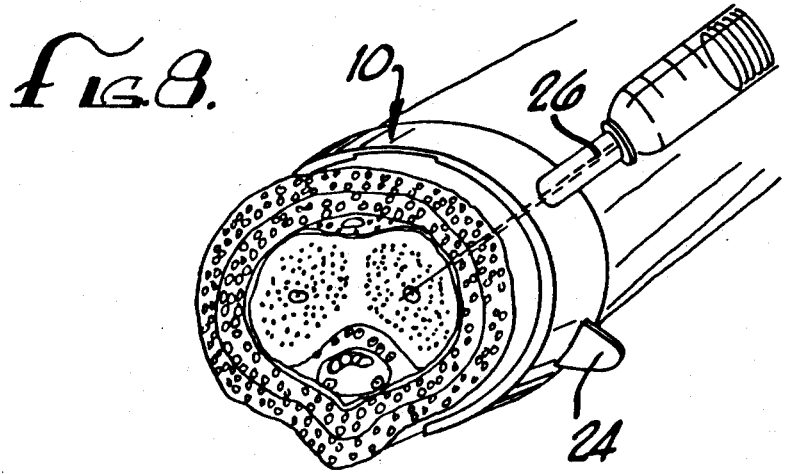
FIG. 8 is a perspective view of the ring of FIG. 1 mounted on the penis during delivery of drugs.

To deliver the erectile stimulus the ring is placed on the penis close to the abdomen with the brake 18 straddling the urethra which runs along the center of the bottom of the penis, as shown in FIG. 8. If the syringe embodiment is used the ring is placed so that the needle guide projects away from the abdomen. In its preferred form a syringe needle placed in the needle guide penetrates the outer skin of the penis and enters the erectile tissue without penetrating any of the surrounding tissue or exiting the erectile tissue. Erection stimulating drugs delivered to other than the erectile tissue is ineffective in creating an erection and may cause an extremely uncomfortable burning sensation in the penis.

Figure 7:
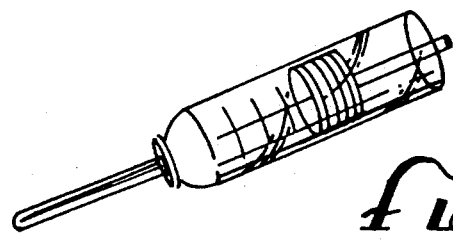
FIG. 7 is a side view of a prefilled drug delivery capsule for use in the ring of FIG. 1.

FIG. 7 shows an example of a disposable drug delivery ampule for use with the ring 10 shown in FIGS. 1 and 2. FIG. 8 shows the ampule of FIG. 7 installed in a syringe in use during delivery of a bolus of drug using the extension tube 26 located on the right side of the ring 10. However, the syringe shown is merely representative of a drug delivery device suitable for use with the invention. Various different disposable or reusable syringes known to the art or developed in the future may be utilized to inject the desired drugs into the penis. The preferred drug delivery device will utilize a small diameter needle (preferably an 18 to 24 gauge needle) which can be placed in the erectile tissue with a minimum of pain or sensation to the user. After syringe delivery of the erection inducing drug the ring can be removed from the penis. Erection can usually be maintained for 2 to 3 hours without additional administration of the stimulant. Use of the ring with needle guide embodying the invention is an extremely effective, accurate and controllable method of creating a penile erection on demand without many of the hazards and inconsistencies of the prior art techniques.

The ring may be constructed from any of a variety of metals or plastics and may be either reusable or disposable. Suitable materials include stiff but flexible plastic materials such as polyethylene, polypropylene, or other similar materials. Suitable dimensions for the ring are ½ to 2 inches in diameter, ¼ to 1 ½ inches in width and at least about 1/32nd inches in thickness. The preferred width is about 1 inch. The rings are usually made in several different diameters to snugly fit the diameter of the flaccid penis of the user which may vary in diameter. The tubes may be about ¼ to about 2 inches in length having an inner diameter sized for easy placement of the preferred syringe needle.

Although the present invention has been described in considerable detail with reference to certain preferred versions and uses thereof, other versions and uses are possible. Therefore, the spirit and scope of the appended claims should not be limited to the description of the preferred versions contained herein.

What is claimed is:

1. A device for delivery of a stimulus to the penis to treat impotence comprising:
   a ring sized to partially but substantially encircle and contact, along the ring's entire inner surface, the penis of a human male,
   the ring having a break and a flexible portion located between said first and second ends,
   said ring having a uniform thickness with said flexible potion being of a reduced area of thickness therein and first and second ends spaced from each other on opposite sides of the break,
   the ring being flexible so that the circumference of the ring can be manually increased by bending or by expansion of the penis,
   the ring adapted for delivery of a stimulus to cause erection of the penis after placement of the ring thereon.

2. The device of claim 1 further having first and second placement means located between the flexible portion and the first and second ends.

3. The device of claim 2 wherein the first and second placement means are tabs sized for grasping between the users fingers, the tabs extending from the outer surface of the ring.

4. The device of claim 1 wherein the inner surface of the ring is at least partially coated with a skin compatible adhesive.

5. The device of claim 1 wherein the ring has at least one hole formed through its thickness and a needle guide placed over each hole, said needle guide projecting from the outer surface of the ring at an angle to the surface.

6. The device of claim 5 wherein the needle guide projects from the ring surface at an angle of about 10 degrees to about 75 degrees, said needle guide projecting toward the edge of the ring.

7. The device of claim 6 wherein the needle guide projects at an angle of about 20 to 45 degrees from the ring surface along a plane perpendicular to the edges of the ring.

8. The device of claim 5 wherein the needle guide is a tubular extension chosen to receive a small diameter hypodermic needle.

9. The device of claim 1 wherein the inner surface of the ring is coated with a material capable of dispensing a drug deliverable transcutaneously.

10. The device of claim 1 wherein the inner surface of the ring is coated with an electrically conductive material.

11. A device to aid in the delivery of an erection inducing drug to the penis comprising:
    a flexible ring sized to partially encircle a flaccid penis,
    the ring having a break therein to aid in properly placing the ring on the flaccid penis and at least one needle guide extending from its surface, said needle guide located above the penile erectile tissue and the break straddling the urethra when properly placed on the penis, the needle guide being angled and oriented so that a syringe needle placed through the needle guide penetrates through the covering skin and into the erectile tissue without penetrating other surrounding tissue.

12. A syringe placement guide for delivery of an erection inducing drug to the penis comprising:
    a flexible ring having a flat outer surface and a flat inner surface bounded by two edges and a break extending across the width of the ring and through the edges,
    a needle guide projecting at an angle to the outer surface of the the needle guide projecting at an angle to the outer surface of the ring and extending over one of the edges of the outer surface
    the needle guide being located over the penile erectile tissue and the break straddling the urethra when properly placed on the penis.

13. The syringe placement device of claim 12 further having grasping means extending from the ring to aid in placing the ring on a flaccid penis.

14. The syringe placement device of claim 12 further having an adhesive material coating the inner surface of the ring.

15. The syringe placement device of claim 12 wherein the ring has a width of about ¼ to 1 ½ inches, a diameter of about ½ to 2 inches and a thickness greater than about 1/32 of an inch.

16. The syringe placement device of claim 12 wherein the needle guide projects from the ring surface at an angle of about 15 to 45 degrees.